(12) United States Patent
Buhring et al.

(10) Patent No.: US 8,163,495 B2
(45) Date of Patent: Apr. 24, 2012

(54) METHOD FOR ISOLATING AND/OR IDENTIFYING MESENCHYMAL STEM CELLS (MSC)

(75) Inventors: Hans-Jorg Buhring, Tuebingen (DE); Reiner Lammers, Tuebingen (DE); Sabrina Treml, Bodelshausen (DE); Venkata Lokesh Battula, Tuebingen (DE)

(73) Assignee: Eberhard-Karls-Universität Tuebingen Universitaetsklinikum, Tuebingen (DE)

( * ) Notice: Subject to any disclaimer, the term of this patent is extended or adjusted under 35 U.S.C. 154(b) by 1199 days.

(21) Appl. No.: 11/853,604

(22) Filed: Sep. 11, 2007

(65) Prior Publication Data

US 2008/0075699 A1 Mar. 27, 2008

(30) Foreign Application Priority Data

Sep. 12, 2006 (DE) .......................... 10 2006 043 625

(51) Int. Cl.
*G01N 33/53* (2006.01)
*C12N 5/00* (2006.01)
*C12N 5/071* (2010.01)
(52) U.S. Cl. .......................... 435/7.1; 435/372; 435/374
(58) Field of Classification Search .......................... None
See application file for complete search history.

(56) References Cited

U.S. PATENT DOCUMENTS

| 6,087,113 | A | * | 7/2000 | Caplan et al. | ................... | 435/7.1 |
| 7,364,863 | B2 | * | 4/2008 | Buhring et al. | ................ | 435/7.1 |
| 2002/0051785 | A1 | | 5/2002 | Slamon et al. | | |
| 2005/0214873 | A1 | | 9/2005 | Buehring et al. | | |

FOREIGN PATENT DOCUMENTS

| DE | DE 102 42 338 A1 | 3/2004 |
| EP | 1 365 034 A2 | 11/2003 |

OTHER PUBLICATIONS

Bühring et al., "Novel Markers for the Prospective Isolation of Human MSC," *Ann. N.Y. Acad. Sci.*, 1106:262-271, 2007.
Jamoulle "Follicular Penetration and Distribution of Topically Applied CD 271, a New Naphthoic Acid Derivative Intended for Topical Acne Treatment," *Journal of Investigative Dermatology*, "Abstract," 731-732, 1990.
European Search Report from related European Patent Application No. 07017866.0, 8 pages, dated Jul. 8, 2009.
Barry et al., "The SH-3 and SH-4 Antibodies Recognize Distinct Epitopes on CD73 from Human Mesenchymal Stem Cells," *Biochemical and Biophysical Research Communications*, vol. 289, Elsevier Science, 2001, (pp. 519-524).
Gregory et al., "Non-hematopoietic bone marrow stem cells: Molecular control of expansion and differentiation," *Experimental Cell Research*, vol. 306, Elsevier, 2005, (pp. 330-335).
Horwitz et al., "Position Paper Clarification of the nomenclature for MSC: The International Society for Cellular Therapy position statement," *International Society for Cellular Therapy*, IASCT, vol. 7, No. 5, Taylor & Francis, 2005, (pp. 393-395).
Leucocyte Typing V, White Cell Differentiation Antigens, Schlossman SF et al., CD Guide Appendix, CD56 selected reference, 1993, (p. 2012).
Pittenger et al., "Multilineage Potential of Adult Human Mesenchymal Stem Cells," *Science*, vol. 284, Apr. 2, 1999, (pp. 143-147).
Quirici et al., "Isolation of bone marrow mesenchymal stem cells by anti-nerve growth factor receptor antibodies," *International Society for Experimental Hematology*, vol. 30, Elsevier, 2002, (pp. 783-791).
Vogel, et al., "Heterogeneity among human bone marrow-derived mesenchymal stem cells and neural progenitor cells," *Journal of Hemotology*, vol. 88, No. 2, Feb. 2003, (pp. 126-133).

\* cited by examiner

*Primary Examiner* — Michail Belyavskyi
(74) *Attorney, Agent, or Firm* — Klarquist Sparkman, LLP (57) ABSTRACT

The present invention concerns antibodies produced from hybridoma cell lines chosen from the group comprising W8B2, W1C3, W7C6, W5C4, 24D2, 28D4, HEK-3D6, W4A5, W3D5, W5C5, 9A3G9, 58B1, F9-3C2F1, 39D5, for isolating and/or identifying homogenous mesenchymal stem cells. Furthermore a method is presented with which mesenchymal stem cells from adult primary tissue, for example bone marrow, can be identified and isolated with a high level of purity.

18 Claims, 7 Drawing Sheets

Morphology of W8B2B10+ Bone Marrow Cells on day 10 of cultivation

METHOD FOR ISOLATING AND/OR IDENTIFYING MESENCHYMAL STEM CELLS (MSC)

CROSS-REFERENCES TO RELATED APPLICATIONS

This application claims priority of German Patent Application DE 10 2006 043 625.3, filed on Sep. 12, 2006.

BACKGROUND OF THE INVENTION

The present invention concerns a method for prospectively isolating and/or identifying mesenchymal stem cells.

The term "mesenchymal stem cells" (MSC) is not uniformly defined in the literature. In principle there are two distinct types of cells: MSC which are isolated directly from non-hematopoietic primary tissue (e.g. bone marrow, adipose tissue, placenta), and cells which differentiate in culture from these primary cells into adherent, fibroblast cells and there express cell surface markers, such as CD73, CD105, CD166, but are negative for the hematopoietic stem cell marker CD34 and the pan-leukocyte marker CD45. In general, cells generated in culture are known as mesenchymal stem cells, as after this process they themselves possess a multipotent capacity to differentiate. Just recently however the International Society for Cellular Therapy has brought out a position statement compiled with the aim of standardizing the nomenclature for these cells (Horwitz E M et al., "Clarification of the nomenclature for MSC: The International Society for Cellular Therapy Position Statement", Cytotherapy 2005:7; 393-395). In this publication, cells from primary tissue that have the ability to form fibroblast colonies in culture (colony forming unit fibroblast=CFU-F) are described as mesenchymal stem cells (MSC). In contrast, adherent cells with fibroblastoid morphology which are generated by culturing cells from primary tissue are known as "multipotent mesenchymal stromal cells". The acronym "MSC" has however likewise been retained for these cells.

Owing to their multipotency, i.e. their ability in suitable in vitro and in vivo conditions to differentiate into different mesenchymal tissues (such as bone, fat, muscle, cartilage, etc.), mesenchymal stem cells are already being used therapeutically. Thus for example, MSCs isolated from umbilical cord blood, bone marrow and adipose tissue that are capable of differentiation can be expanded in vitro and differentiated into osteoblasts, chondrocytes and myocytes, and then be used again in vivo for example for regenerating bones, cartilage, tendons, muscles and adipose tissue, as well as stroma.

Besides the ability to adhere rapidly and with stability to plastic or glass surfaces, MSC (multipotent mesenchymal stromal cell) phenotypes are characterized by their fibroblastoid morphology and by their expression (for example, of CD73, CD90, CD105, CD166) and/or lack of expression (of CD34, CD45). Many of the surface molecules expressed on MSC can also be found on endothelial and epithelial cells and on muscle cells. On the other hand, however, MSCs are clearly distinct from hematopoietic stem cells as they do not express any specific hematopoietic markers such as CD45, for example.

RELATED PRIOR ART

It is known from the prior art that mesenchymal stem cells can be isolated from bone marrow using antibodies directed against the low-affinity nerve growth factor receptor (=CD271) (Quirici et al., "Isolation of bone marrow mesenchymal stem cells by anti-nerve growth factor receptor antibodies". Exp. Hematol., 2002, 30(7):783-791). Furthermore, it has been described how MSC can be isolated using antibodies to SH2 (CD105), SI-3 (CD73) and SH4 (CD73) (see Barry F. et al. "The SH-3 and SH-4 antibodies recognize distinct epitopes on CD73 from human mesenchymal stem cells", Biochem Biophys Res Commun. 2001; 289:519-24 and Pittenger M F. et al., "Multilineage potential of adult human mesenchymal stem cells", Science. 1999; 284:143-7). However, the disadvantage of the present markers is that they are not specific to MSC but recognize other cell populations in bone marrow.

Vogel et al. (Vogel W. et al., "Heterogeneity among human bone marrow-derived mesenchymal stem cells and neural progenitor cells", Haematologica, 2003, 888:126-133) describe moreover the antigen defined by the antibody W8D2 as a new marker that is very heterogeneously expressed on cultured MSC.

The cell surface marker CD271 has until now been the most specific commercially available cell surface marker for isolating mesenchymal stem cells. Monoclonal antibodies to this marker, for example, are therefore marketed by the companies BD PharMingen, San Diego, USA and Miltenyi Biotec, Bergisch Gladbach, Germany. However it has come to light that this marker is not selective for MSC but is also expressed on other CD45-positive hematopoietic cells. As a result, in an isolation method with anti-CD271 antibodies, not only mesenchymal but also hematopoietic cells are isolated.

Against the background of the disadvantages recognized from the prior art, it is an object of the present invention to provide new possibilities for isolating as far as possible pure mesenchymal stem cells (MSC) from primary tissues.

SUMMARY OF THE INVENTION

As claimed in the present invention, this object is achieved by means of antibodies or functional fragments thereof being made available for isolating and/or identifying homogenous mesenchymal stem cells from primary tissues generated from hybridoma cell lines, the latter selected from the group comprising W8B2, W1C3, W7C6, W5C4, 24D2, 28D4, HEK-3D6, W4A5, W3D5, W5C5, 9A3G9, 58B1, F9-3C2F1 and 39D5, which have been deposited at the German Collection of Microorganisms and Cell Cultures (DSMZ) in accordance with the Budapest Treaty, and/or published or are commercially available.

Moreover, the object is achieved by means of a method for identifying and/or isolating homogenous mesenchymal stem cells that involves the following steps:

putting a sample of a cell suspension of primary tissue containing mesenchymal stem cells into contact with at least one antibody or fragment thereof produced from the hybridoma cell lines W8B2, W1C3, W7C6, W5C4, 24D2, 28D4, HEK-3D6, W4A5, W3D5, W5C5, 9A3G9, 58B1, F9-3C2F1 and 39D5;

identification and/or isolation of the cells in the sample that have bound to the antibodies in step a).

In addition, the invention also relates to the antibodies that are used for this isolation/identification of mesenchymal stem cells, and which are generated from one of the hybridoma cell lines designated as W1C3, W7C6, W5C4, HEK-3D6, W4A5, W3D5, W5C5, 9A3G9, 58B1, F9-3C2F1 or 39D5, which have been officially deposited at the German Collection of Microorganisms and Cell Cultures (DSMZ) in accordance with the Budapest Treaty.

The object of the invention is completely met in this way.

The inventors knew that with the mentioned antibodies it is possible to isolate ultra-pure homogenous MSC subpopulations, for example directly from bone marrow, and consequently directly from primary tissue. Thus for example, a subset of CD271-positive cells containing exclusively MSC was able to be identified by double fluorescence analysis from a CD271-positive pool of cells by means of the antibodies as claimed in the invention. Only the antibody-positive fraction contained clonogenic mesenchymal stem cells, i.e. they had the ability to form CFU-F.

As has been mentioned earlier, it was not previously possible to isolate ultra-pure mesenchymal stem cells from primary tissues. The technique was known in the prior art, as mentioned above, merely of how to isolate and identify MSC cells by culturing cells from primary tissue, that is to say adherent cells with fibroblastoid morphology that express the surface markers such as CD73, CD105, CD166 and are described as multipotent mesenchymal stromal cells.

With the mentioned antibodies, new tools are available for identifying MSC, as these antibodies are specific for antigens that recognize the cell-bound, extracellular domains of plasma membrane proteins which are highly selectively expressed on MSC. Such antibodies are therefore appropriate for targeting, i.e. living cells can be isolated and subsequently cultured, or (tumor) cells can be eliminated.

These results were utterly surprising as until now mesenchymal stem cells could not be produced with such a great degree of purity. With the new antibodies, an extremely pure MSC population can thus be prepared which can be used for example for cell and gene therapy.

With the new method for using the antibodies it is therefore possible to clearly improve the techniques acknowledged from the prior art for isolating/identifying mesenchymal stem cells, since it is only possible to obtain ultra-pure and homogenous MSC subpopulations with the method as claimed in the invention and the new antibodies as claimed in the invention used therein.

In the context of the present invention, instead of the respective antibody claimed, a fragment of the antibody which has the same labeling characteristics as the complete antibody can also be used, without this being expressly stated in each case. "Functional fragment" means in this case any fragment of an antibody that contains the antigen binding function of the antibody. Such fragments are for example $F_{ab}$, $F_{(ab')2}$, $F_v$ and other fragments such as CDR fragments. The fragments mentioned have the binding specificity of the antibody and can also be produced for example with known methods.

The possibility exists, furthermore, of using humanized antibodies derived from the mentioned antibodies. As the constant part of antibodies in pure mouse antibodies is murine, such antibodies, if for example they were to be used in humans, might lead to reactions involving rejection by the immune system. Besides specificity to human antigens residing in the variable region, mouse monoclonal antibodies which have been generated against a human antigen contain mouse antigen domains, which may be rejected by the human immune system as foreign. The murine parts of the constant sections can therefore be eliminated by methods used in molecular biology and be replaced by structurally constant parts of human antibodies. The constant sections of antibodies are not involved in the specific binding of the monoclonal antibody. The monoclonal antibody thus arising is called a "humanized monoclonal antibody" and is no longer rejected by the human immune system. Humanized antibodies are produced for example, in a culture of hamster ovarian cells. (Concerning generating humanized antibodies, see for example Sharon et al., Nature 309: 364-367, 1984). It will consequently now be clear to the specialist that the mouse antibodies described here for the first time can be modified by pertinent molecular biology methods for use in humans, even for instance by exchanging the constant regions of mouse antibodies for human constant regions.

It is to be understood that the antibodies as claimed in the invention can also be variously marked/conjugated, depending on use or desired use in relation to the detection method, for example with chemical reagents. These kinds of modification of antibodies are within the sphere and ability of the specialist in the field.

In a further embodiment of the invention, the primary tissue is chosen from the group including bone marrow, adipose tissue and placenta. It is well known that these tissues contain mesenchymal stem cells. These cells, or the sample containing cells, are obtained as claimed in the laboratory methods and extraction techniques known in the prior art.

Antibodies produced from the hybridoma cell line 24D2 are directed against HER2 (CD340). The HER2 gene encodes a member of the receptor tyrosine kinase epidermal growth factor (EGF) receptor family. The antibody produced through the hybridoma cell line 24D2 can be commercially obtained for example from the company Santa Cruz, Calif., USA. Antibodies produced from the hybridoma cell line 28D4 are directed against the antigen CD140b and can be obtained for example from the company BD Biosciences PharMingen.

The antibodies produced with the hybridoma cell line known as 39D5 are directed against CD56 (Leukocyte Typing V, White cell differentiation antigens. Schlossman S F et al.; 1993; p. 2012). Unlike the other antibodies with specificity for CD56, 39D5 is the only one not to recognize any NK cells in the peripheral blood and bone marrow. It therefore reacts highly specifically with a distinct MSC subpopulation. Several anti-CD56 antibodies are commercially available from the company antibodies-online GmbH, Aachen, Germany, or from Kamiya Biomedical Company, Seattle, USA; or from eBioscience, San Diego, U.S.A.

With regard to their suitability for isolating/identifying mesenchymal stem cells as described herein, the antibodies, the antigens of which have already been identified, i.e. 24D2 (CD340), 28D4 (CD140b) and 39D5 (CD56) and which can in part be obtained commercially, have not yet been described. The new property established by the inventors is almost completely unexpected and offers the possibility of using already known antibodies for a new use in a new method.

The fact that the named antibodies that are already commercially available have a characteristic making them suitable for isolating/identifying ultra-pure mesenchymal stem cells from primary tissue has not until now been described, nor even known, in the prior art.

The claimed antibodies W8B2, W1C3, W7C6, W5C4, HEK-3D6, W3D5, W5C5, 9A3G2, W4A5, 58B1, F9-3C2F1 (also designated F9-3C2), are produced by the hybridoma cell lines which are deposited, in accordance with the Budapest Treaty, at the Deutsche Sammlung von Mikroorganismen and Zellkulturen (DSMZ) (Zellkulturen GmbH, Inhoffenstraβe 7 B, 38124 Braunschweig, Germany) under the numbers DSM ACC 2567 (W8B2) and DSM ACC 2571 (W4A5) on Aug. 14, 2002; DSM ACC 2816 (W1C3), DSM ACC 2821 (W7C6), DSM ACC 2814 (W5C4), DSM ACC 2817 (HEK-3D6), DSM ACC 2815 (W3D5), DSM ACC 2813 (W5C5), DSM ACC 2820 (9A3G2), DSM ACC 2819 (58B1), DSM ACC 2818 (F9-3C2) on Feb. 21, 2007. All restrictions on the availability to the public of the material so deposited will be irrevocably removed upon the granting of a patent. However, it should be understood that the availability of a deposit does not constitute a license to practice the subject invention in derogation of patent rights granted by governmental action.

Even the antibodies published here for the first time, and hybridoma cell lines producing them, like the previously mentioned antibodies, have the advantageous characteristic of being suitable for isolating/identifying ultra-pure mesenchymal stem cells from primary tissue.

In further embodiments an antibody is used moreover, that binds to the same anti-gen as an antibody produced from the hybridoma cell lines W8B2, W1C3, W7C6, W5C4, 24D2, 28D4, HEK-3D6, W4A5, W3D5, W5C5, 9A3G9, 58B1, F9-3C2F1, 39D5.

With the antibodies prepared by the inventors, it is possible to precisely characterize and identify the respective antigens on the MSCs, which in turn makes it possible to selectively generate antibodies to the antigens thus determined. These may then be used in turn in the method as claimed in the invention for isolating MSCs.

In the method as claimed in the invention, putting a sample into contact with a suspension of cells including mesenchymal cells may be performed in solution, as is the case for example when using a fluorescence-activated cell sorter (FACS).

In flow cytometry, cells labeled with fluorochrome-conjugated antibodies are analyzed and individually sorted. It can thus be established therefore which fraction of a cell population is positive for a given marker.

A method for magnetic cell separation may also be used (MACS: magnetic activated cell sorting). In this method the cells are separated using antibodies to which magnetic beads are coupled.

The mesenchymal stem cells identified/isolated in this way can then be used for example for a transplantation in order to achieve regeneration of for example damaged bone, cartilage etc.

It is further possible to use the antibodies or their humanized derivatives for coating medical implants or medical devices like stents and to use such treated implants or devices for treating diseased or defect or damaged tissue, cartilage or bone.

In a further preferred embodiment of the method as claimed in the invention the sample including heterogeneous mesenchymal stem cells is brought into contact with an antibody which is generated from hybridoma cell lines chosen from the group including W8B2, W1C3, W7C6, W5C4, 24D2, 28D4, HEK-3D6, W4A5, W3D5, W5C5, 9A3G9, 58B1, F9-3C2F1, 39D5, and with an anti-CD271 antibody; subsequently, such cells in the sample that have bound to both antibodies, or fragments of them, can then be isolated or identified. The anti-CD271 antibody and the antibodies as claimed in the invention preferably exhibit distinct color/fluorescence labeling. In the method as claimed in the invention the anti-CD271 antibody and at least one of the new antibodies as claimed in the invention are used therein simultaneously or successively.

The invention also concerns hybridoma cell lines that have the ability to generate and release these kinds of antibodies, and particularly the hybridoma cell lines W1C3, W7C6, W5C4, HEK-3D6, W4A5, W3D5, W5C5, 9A3G9, 58B1, F9-3C2F1, 39D5 (DSM ACC 2530), which have been officially deposited at the German Collection of Microorganisms and Cell Cultures (DSMZ, Zellkulturen GmbH, Inhoffenstraβe 7 B, 38124 Braunschweig, Germany) on Jul. 8, 2008 (39D5), on Aug. 14, 2002 (W4A5), and on Feb. 21, 2007 (W1C3, W7C6, W5C4, HEK-3D6, W3D5, W5C5, 9A3G9, 58B1, F9-3C2F1), in accordance with the Budapest Treaty.

All restrictions on the availability to the public of the material so deposited will be irrevocably removed upon the granting of a patent. However, it should be understood that the availability of a deposit does not constitute a license to practice the subject invention in derogation of patent rights granted by governmental action.

For the first time, the inventors have produced monoclonal antibodies with the new antibodies as well as hybridoma cell lines, generating and releasing these which enable selective recognition of mesenchymal stem cells. The antibodies consequently represent a hitherto unbelievable means for the doctor and researcher firstly of detecting these kinds of cells and secondly of manipulating these cells as necessary, either via the antibodies themselves or via reagents coupled to them. The antibodies W1C3, W3D5, W4A5, W5C4, W5C5, W7C6 and W8B2 were obtained by immunization with the retinoblast cell line WERI-RB-1. In addition the antibodies HEK-3D6 and F9-3C2F1 were obtained by immunization with the embryonic kidney cell line HEK. The antibody 58B1 was obtained by immunization with the hematopoietic cell line UT-7. The antibodies 24D2 and 28D4 were obtained by immunization with NIH-3T3 cells which were transfected with human HER-2 or PDGF receptor beta. The antibody 9A3G9 was obtained by immunization with the breast carcinoma cell line DU.4475.

The invention also concerns a pharmaceutical composition containing one or more of the above-mentioned antibodies as claimed in the invention, or functional fragments thereof or humanized derivatives thereof.

Such a pharmaceutical composition may contain, besides the one or more antibodies, other appropriate substances, for example diluents, solvents, stabilizers etc. Included among these are for example physiological saline solutions, water, alcohols and other suitable sub-stances which are to be found for example in A. Kibble, "Handbook of Pharmaceutical Excipients", 3rd ed. 2000, American Pharmaceutical Association and Pharmaceutical Press. The pharmaceutical composition is suited for treating diseases or damages which require or can be treated with binding of the antibodies to mesenchymal stem cells.

The invention also concerns a kit that contains at least one of the new antibodies, and a kit that besides at least one of the new antibodies as claimed in the invention has an anti-CD 271 antibody.

The invention also concerns the use of homogenous mesenchymal stem cells obtained following the method as claimed in the invention for producing a medicinal product for gene or cell therapy.

The homogenous mesenchymal stem cells obtained as claimed in the method as claimed in the invention may be used to advantage as cell therapies. In this case the cells should replace a patient's defective or deteriorated tissue or cells, for example damaged bone or cartilage tissue. Following their being introduced and, if necessary, the administration of other differentiation factors, the mesenchymal stem cells differentiate in vivo into the types of cells that they are to replace. The mesenchymal stem cells isolated following the method as claimed in the invention may be either directly implanted/administered or be applied to appropriate implants, where by adding the relevant factors they also differentiate before implantation into the cells desired.

In this way bone and cartilage tissue, for example, that has deteriorated, can be advantageously regenerated.

The invention also concerns the use of homogenous mesenchymal stem cells obtained following the method as claimed in the invention for producing osteoblasts, chondrocytes, adipocytes or fibroblasts in vitro.

In this use, the mesenchymal stem cells obtained following the method as claimed in the invention are differentiated into the desired cell type before being introduced into a patient.

The mesenchymal stem cells isolated can be isolated either from the patient who is to be treated accordingly or from another donor.

Further advantages are to be found in the figures attached and in the description.

It is to be understood that the characteristics mentioned above and those yet to be evoked may be used not only in the respective combination stated but also alone or in other combinations, without this falling outside the scope of the present invention.

Examples of embodiments are presented in the attached drawing and are discussed more precisely in the description. The figures show as follows.

EXAMPLE

Material and Methods

Bone marrow mononuclear cells (BM-MNC) were obtained from the femur shaft of patients receiving hip implants. Approx. 25 ml of bone marrow cells were collected and mixed with 5000 U heparin (Sigma-Aldrich). Mononuclear cells were recovered by Ficoll Histopac density gradient fractionation (750×g, 20 min. at room temperature) and remaining erythrocytes were lysed in ammonium chloride solution for 10 min at 4° C.

For the fluorometric analyses monoclonal antibodies or antibody conjugates were used that are produced from the following hybridoma cell lines: W8B2, W1C3, W7C6, W5C4, 24D2, 28D4, HEK-3D6, W4A5, W3D5, W5C5, 9A3G9, 58B1, F9-3C2F1, 39D5. The hybridoma cell line 24D2 produces antibodies directed against HER-2 (CD340), the hybridoma cell line 28D4 antibodies directed against CD140b, and the hybridoma cell line 39D5 antibodies directed against CD56. The hybridoma cell lines W1C3, W3D5 (also designated W3D5A9), W4A5, W5C4 (also designated W5C4W5), W5C5, W7C6 and W8B2 (also designated W8B2B10) producing antibodies were obtained by immunization with the retinoblast cell line WERI-RB-1. The hybridoma cell lines HEK-3D6 and F9-3C2F1 (also designated F9-3C2) were obtained by immunization with the embryonic kidney cell line HEK. The hybridoma cell line 58B1 (also designated 58B1A2) was obtained by immunization with the hematopoietic cell line UT-7. The hybridoma cell lines 24D2 and 28D4 were obtained by immunization with NIH-3T3 cells which were transfected with human HER-2 or PDGF receptor beta. The hybridoma cell line 9A3G9 was obtained by immunization with the breast carcinoma cell line DU.4475.

Another antibody with known specificity, CD271-(LNGFR)-APC was used, obtainable as an APC conjugate in the kit with Anti-APC MicroBeads from Miltenyi Biotec, Bergisch-Gladbach, Germany.

To characterize and isolate MSC, bone marrow cells were first incubated with the antibodies produced from the hybridoma cell lines W8B2, W1C3, W7C6, W5C4, 24D2, 28D4, HEK-3D6, W4A5, W3D5, WSC5, 9A3G9, 58B1, F9-3C2F1 and 39D5 and subsequently labeled with a rabbit anti-mouse antibody conjugated with PE. Cells were then incubated with an excess of mouse IgG (to saturate free valencies) and finally counterstained with a CD271-APC conjugate. After staining cells were analyzed by FACS or fractionated.

Figure 1A:
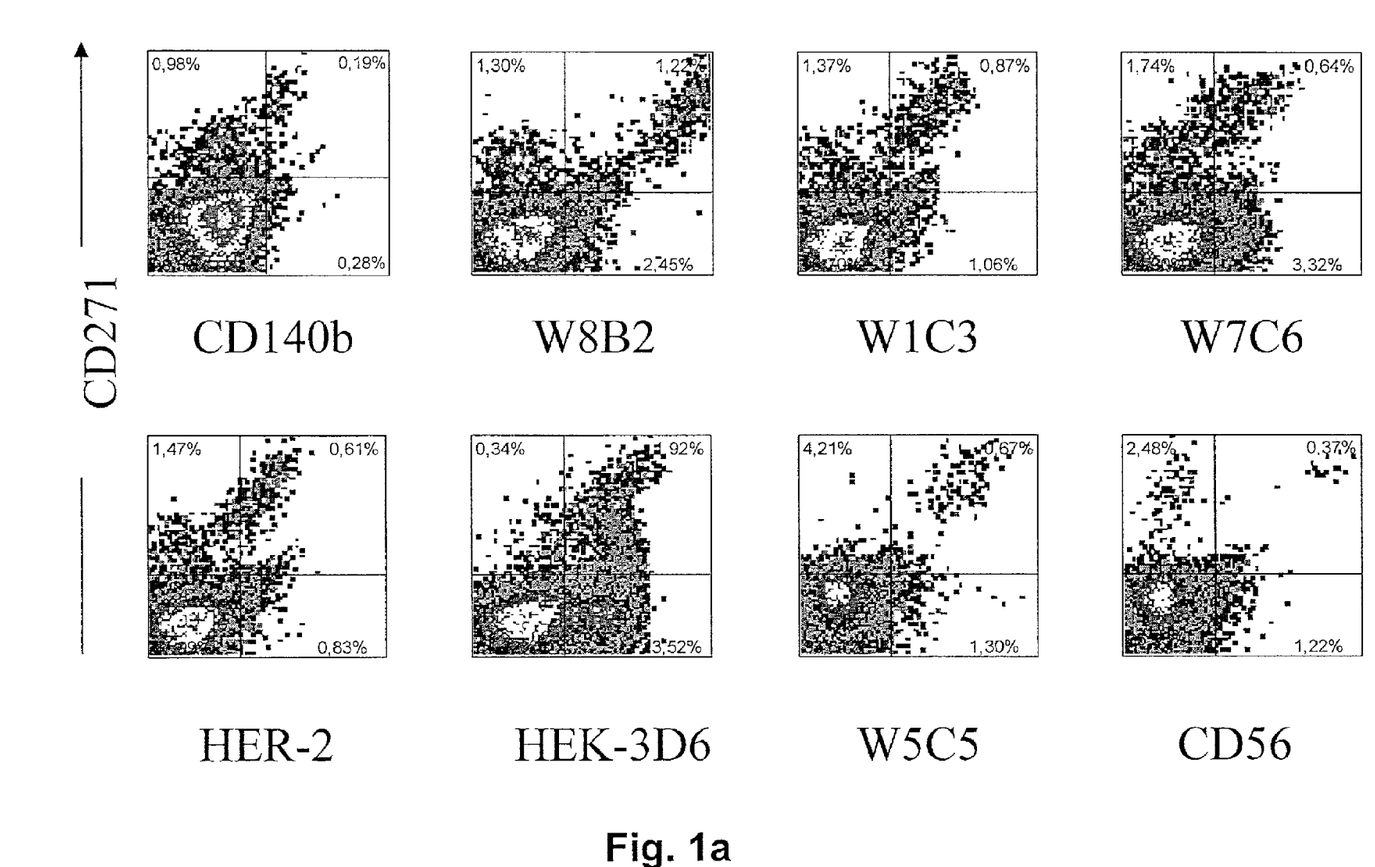
FIG. 1 FACS analyses of bone marrow cells which have been labeled with CD271-APC (Miltenyi Biotech, Germany) and with the antibodies generated by the hybridoma cell lines 28D4, W8B2, W1C3, W7C6, 24D2, HEK-3D6, W5C5, 39D5, (FIG. 1a) and 9A3G9, 58B1, F9-3C2F1, W3D5, W4A5 or W5C4 (FIG. 1b) (indirect labeling with anti-mouse phycoerythrin). Only the antibody-positive fraction (simultaneously positive for CD271) contains MSC with ability to form CFU-F.
Figure 1B:
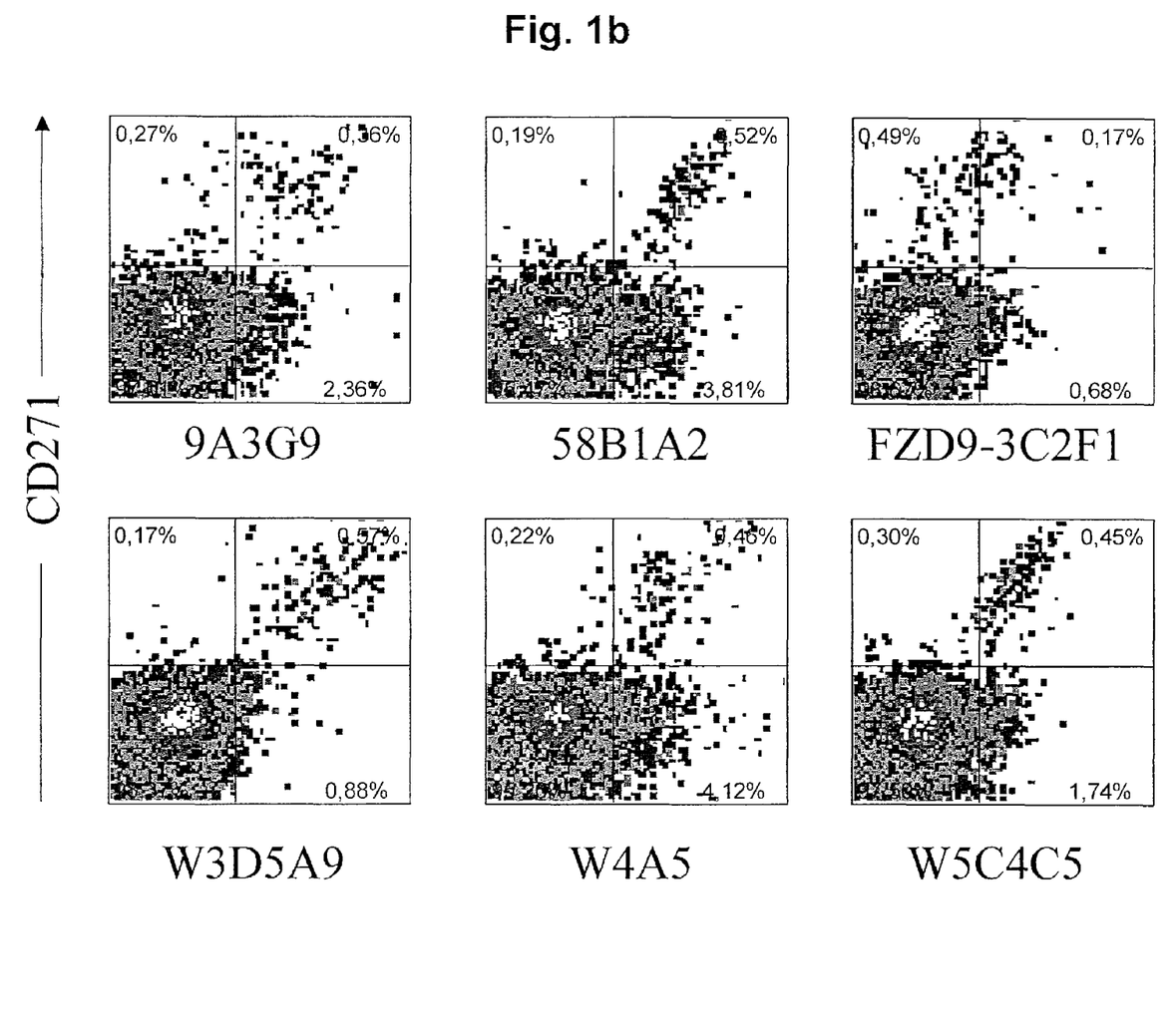

After staining cells were analyzed in the FACSCanto flow cytometer (Becton Dickinson) and evaluated. FIG. 1 shows the respective plots (CD271-APC versus test antibody PE). The antibody-positive cells were then isolated and the ability to form CFU-F determined. As can be seen from the plots in FIG. 1, subpopulations could be isolated and/or identified from the CD271-positive mesenchymal stem cells that were also positive for the particular antibody used. From these subpopulations it could be shown in subsequent assays that clonogenic CFU-F activity was to be found each time in the antibody-positive fraction, while the antibody-negative, CD271-positive fraction was either negative or only contained a few CFU-F.

To perform this assay the cells isolated in the previous steps were cultured in T-25 flasks in serum+gelatin–, serum+gelatin+, serum-gelatin– or serum-gelatin+ conditions. After 14 days culture adherent cells were washed twice with phosphate-buffered saline (PBS), fixed with methanol (5 min. at room temperature) and subsequently dried in air. In order to make the MSC CFU-F visible and count them, the cells were Giemsa-stained (Giemsa solution 1:20 diluted with deionized water; 5 min. at room temperature), washed twice with deionized water and air-dried. CFU-F colonies typically had a diameter between 1 and 8 mm and were evaluated macroscopically.

Furthermore the possibility also exists of differentiating the cells in an alternative way, for example into adipocytes, chondrocytes or osteoblasts. Here priority should be given to the relevant manufacturer's instructions (for example, Miltenyi Biotec). For differentiating MSC into adipocytes and osteoblasts cells were cultured in the presence of either NK AdipoDiff medium or NK OsteoDiff medium (both from Miltenyi Biotec) following the manufacturer's instructions. For this the MSC ($12\times10^4$ cells for adipogenesis; $4.5\times10^4$ cells for osteogenesis) were re-suspended in 1.5 ml of the appropriate medium and transferred to 6-well plates (Falcon, Heidelberg, Germany). The medium was renewed every three days. Adipocyte formation was evaluated on day 18 of the culture by fixing the cells with methanol for 5 min. at –20° C. and by subsequently staining the intracellular lipids with Oil Red O stain (Sigma-Aldrich) for 30 min. at room temperature. Formation of osteogenic cells was analyzed on day 10 of culture by staining the alkaline phosphatase activity of cells fixed with methanol (–20° C., 5 min.) with 5-bromo-4-chloro-3-indolyl phosphate/nitro blue tetrazolium (FAST™ BCIP/NBT substrate; Sigma-Aldrich) for 10 min. at room temperature.

Figure 2A:
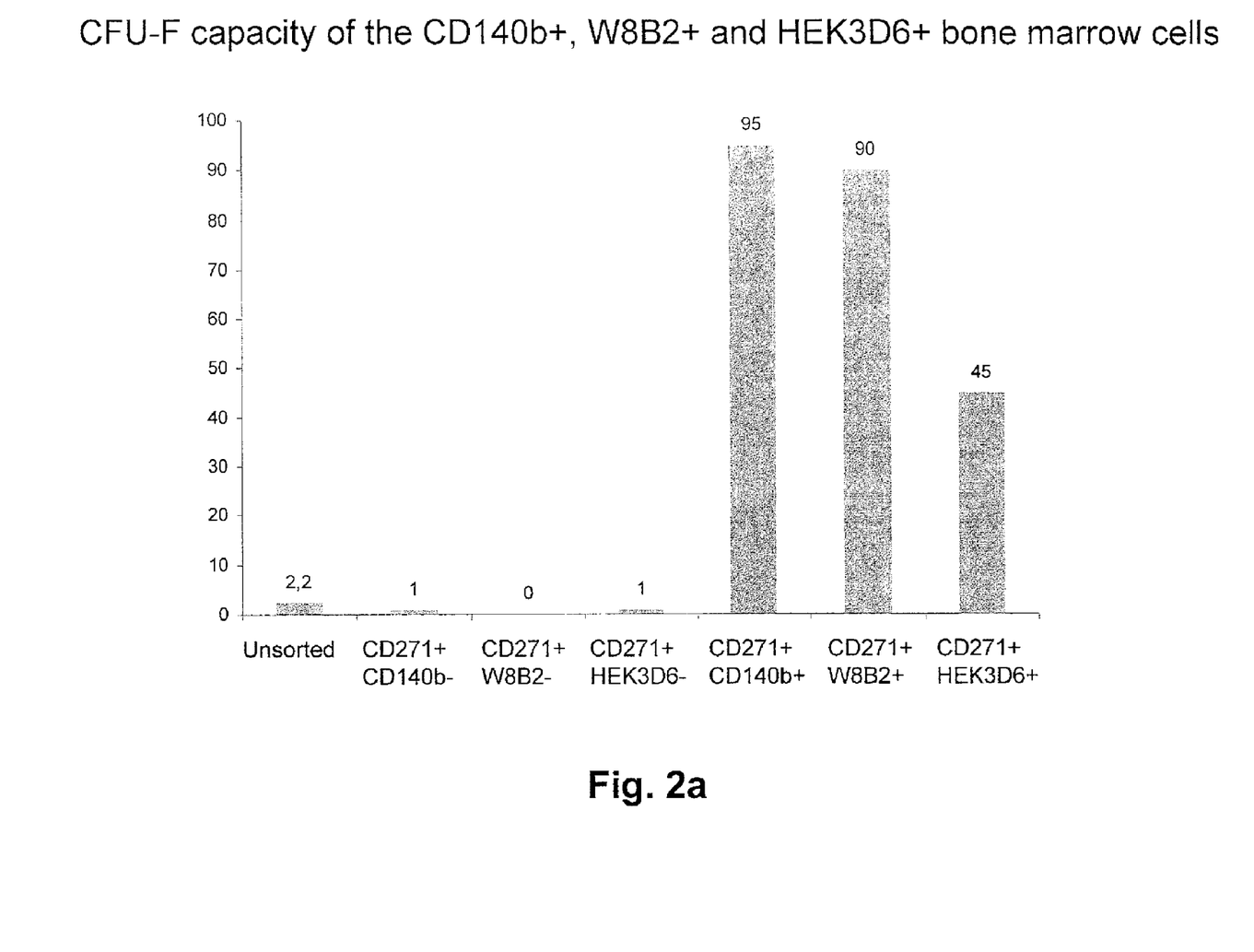
FIG. 2 Bar charts showing the CFU-F activity of sorted CD271+W8B2±, CD271+CD140b±, CD271+HEK3D6± (FIG. 2a) and CD271+CD56± (FIG. 2b) bone marrow cells.
Figure 2B:
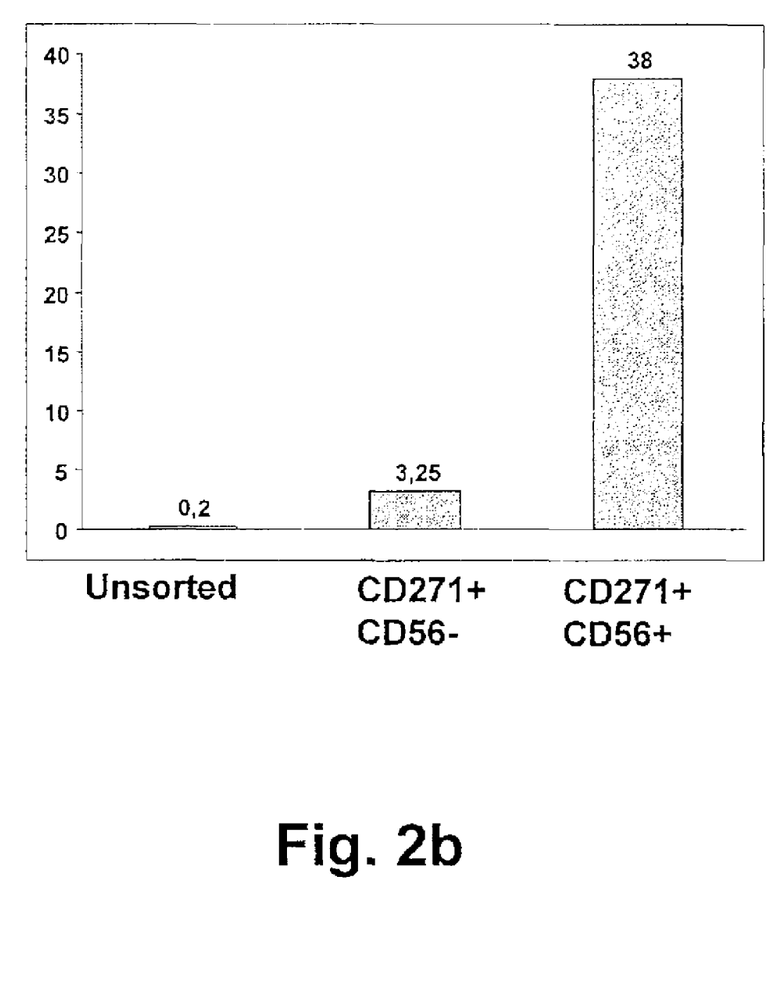

FIG. 2 shows the results of the CFU-F assays for the sorted populations. As can be inferred from FIG. 2a (5000 cells were evaluated here), neither CD271+CD140b– cells nor CD271+

W8B2− cells have significant CFU-F activity. In contrast to this, CD271+CD140b+, CD271+HEK-3D6+ and CD271+W8B2+ cells have strongly enhanced CFU-F activity compared with unsorted cells. Approx. every 50th-100th cell in the positive fractions was an MSC with CFU-F capacity. From FIG. 2b, (500 cells were evaluated here), it can be inferred that CFU-F capacity is clearly higher in the CD271+CD56+ fraction than in the CD271+CD56− fraction. In the double positive fraction, every 10th cell is a CFU-F.

As can be inferred from FIG. 2, CD271-positive but CD140b-negative cells exhibit no or only insignificant CFU-F activity, just like CD271 positive/W8B2-negative cells. On the other hand, CD271 positive/CD140b-positive or W8B2-positive cells exhibit CFU-F activity which distinguishes them as "genuine" mesenchymal stem cells.

Figure 3:
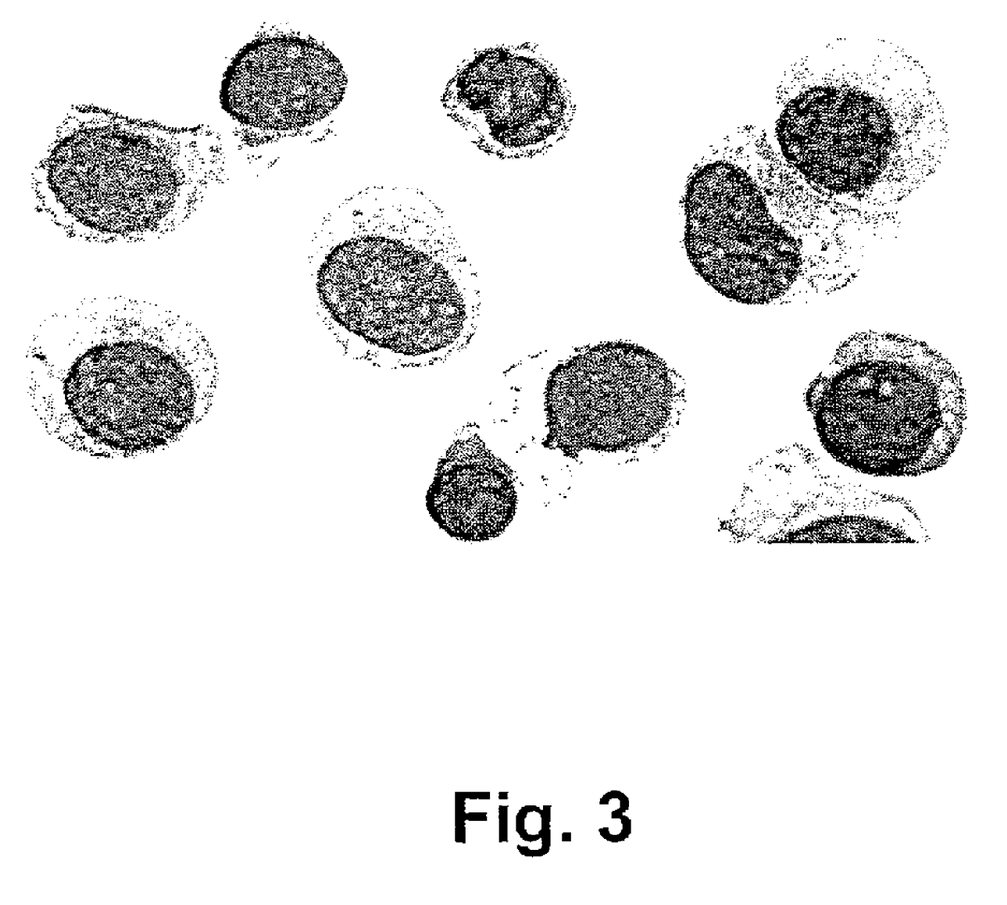
FIG. 3 Cytospin preparation of CD271+W8B2+ sorted MSC from bone marrow. Following preparation the cells were stained with May-Grünwald-Giemsa solution.

FIG. 3 shows, as far as the inventors are aware for the first time in the literature, the morphology of sorted MSC from bone marrow. MSC are distinguished accordingly by having a relatively high proportion of cytoplasm, in which in addition drops of lipids seem to be located. The images were made with a Zeiss Axiovert microscope using the Axiovision software, and evalutated. Magnification: ×100.

Figure 4A:
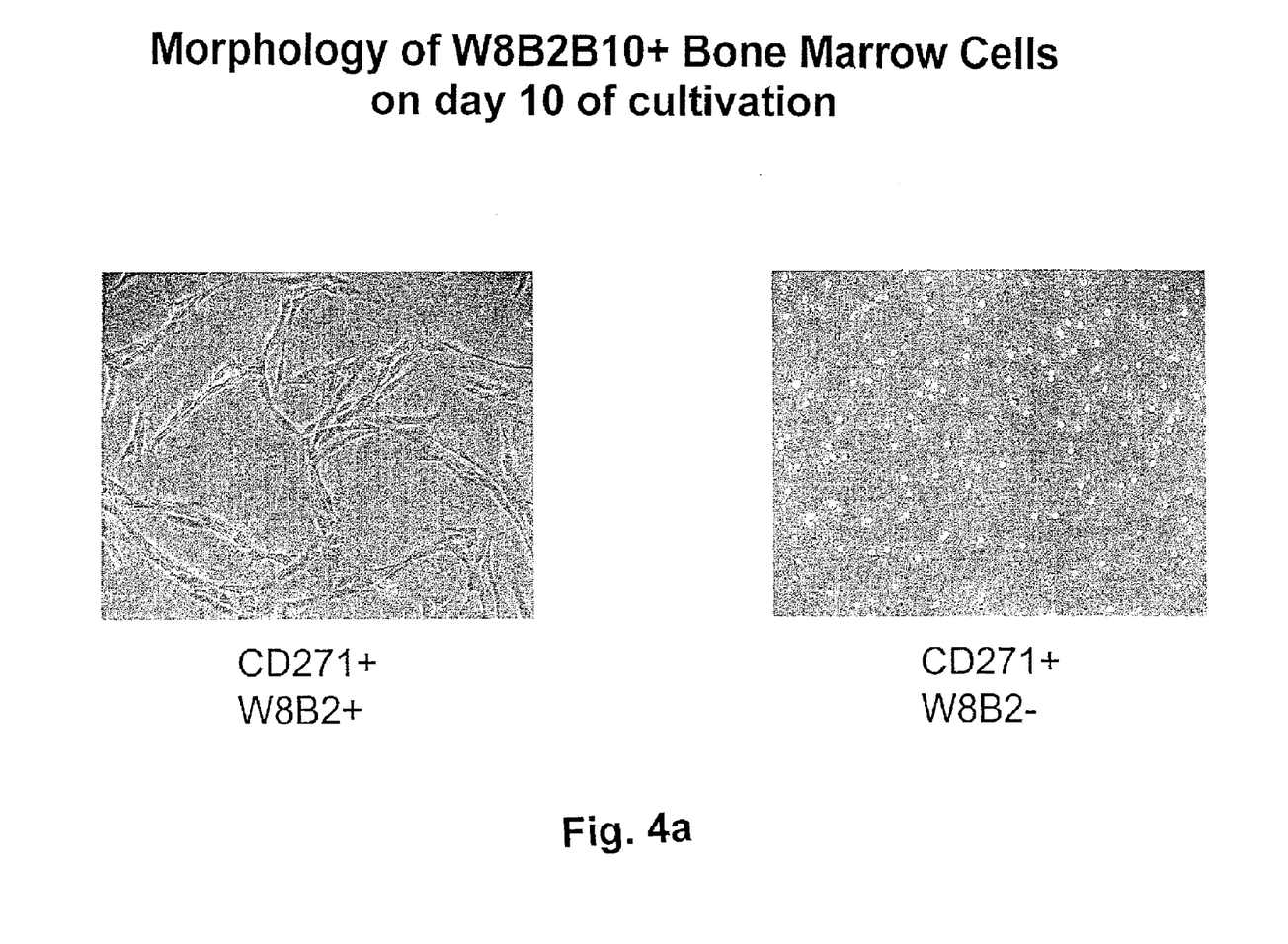
FIG. 4a Microscope images of CD271-positive and W8B2-positive/negative bone marrow cells.
Figure 4B:
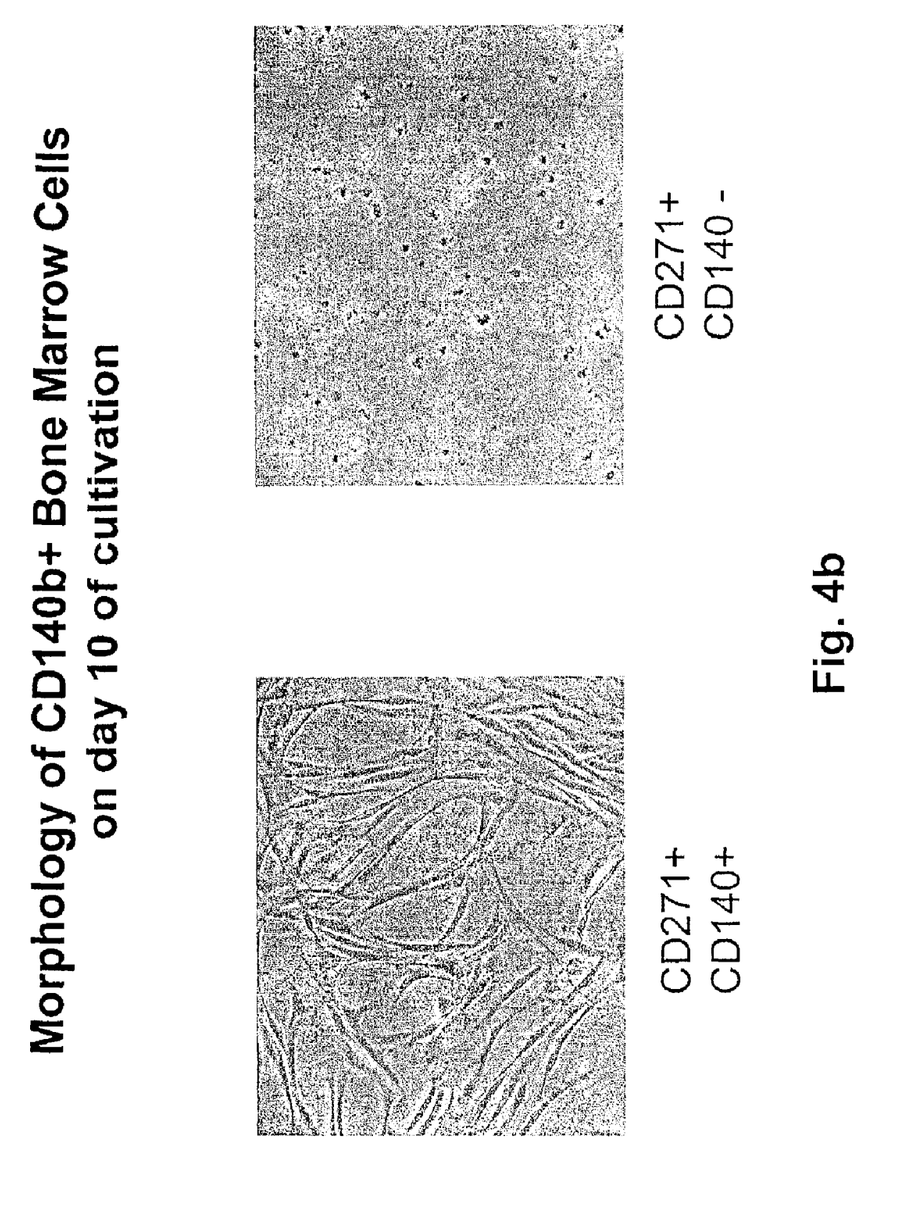
FIG. 4b Microscope images of CD271-positive and CD140b-positive/negative bone marrow cells.

FIG. 4a and FIG. 4b show enlarged images of sorted cells obtained after 10 days in vitro differentiation. The cells were CD271-positive after sorting in each case in both figures. In the left-hand image, FIG. 4a shows cells that were in addition isolated using W8B2, and accordingly express the corresponding antigen. As can be seen from the figures, MSC could only be produced in the culture from cells of the double positive fraction (CD271+W8B2+), not from the CD271+W8B2− fraction. FIG. 4b, like FIG. 4a, shows analog growth behavior for cells of the CD271+CD140b+ fraction.

Therefore, what is claimed, is:

1. A method for isolating and/or identifying homogenous mesenchymal stem cells from primary tissue, which includes the following steps:
   a) putting a sample suspension of cells directly obtained from a primary tissue, and including mesenchymal stem cells, in contact with an antibody, humanized form or antigen binding fragment thereof, wherein the antibody is produced from hybridoma cell lines selected from the group consisting of W1C3 (DSM ACC 2816), W7C6 (DSM ACC 2821), W5C4 (DSM ACC 2814), 24D2, 28D4, HEK-3D6 (DSM ACC 2817), W4A5 (DSM ACC 2571), W3D5 (DSM ACC 2815), W5C5 (DSM ACC 2813), 9A3G9 (DSM ACC 2820), 58B1 (DSM ACC 2819), F9-3C2F1 (DSM ACC 2818), and 39D5 (DSM ACC 2930); and
   b) identifying and/or isolating those cells in the sample to which an antibody from step a), or antigen binding fragment or humanized form thereof have bound, thereby isolating and/or identifying homogenous mesenchymal stem cells.

2. A method for isolating and/or identifying homogenous mesenchymal stem cells from primary tissue, which includes the following steps:
   a) putting a sample suspension of cells directly obtained from a primary tissue, and including mesenchymal stem cells, in contact with an anti-CD271 antibody;
   b) putting the sample from step a) in contact with an antibody, an antigen binding fragment thereof or humanized form thereof, produced from hybridoma cell lines selected from the group consisting of W1C3 (DSM ACC 2816), W7C6 (DSM ACC 2821), W5C4 (DSM ACC 2814), 24D2, 28D4, HEK-3D6 (DSM ACC 2817), W4A5 (DSM ACC 2571), W3D5 (DSM ACC 2815), W5C5 (DSM ACC 2813), 9A3G9 (DSM ACC 2820), 58B1 (DSM ACC 2819), F9-3C2F1 (DSM ACC 2818), and 39D5 (DSM ACC 2930); and
   c) identifying and/or isolating those cells in the sample to which the antibody from step a), and an antibody from step b) or antigen binding fragment or humanized form thereof have bound, thereby isolating and/or identifying homogenous mesenchymal stem cells.

3. The method of claim 2, wherein steps a) and b) are performed simultaneously, successively or in reverse.

4. A method for isolating and/or identifying homogenous mesenchymal stem cells from primary tissue, which includes the following steps:
   a) putting a sample suspension of cells directly obtained from primary tissue and including mesenchymal stem cells in contact with an antibody, humanized form or antigen binding fragment thereof, that binds to the same antigen as an antibody produced from the hybridoma cell lines W1C3 (DSM ACC 2816), W7C6 (DSM ACC 2821), W5C4 (DSM ACC 2814), 24D2, 28D4, HEK-3D6 (DSM ACC 2817), W4A5 (DSM ACC 2571), W3D5 (DSM ACC 2815), W5C5 (DSM ACC 2813), 9A3G9 (DSM ACC 2820), 58B1 (DSM ACC 2819), F9-3C2F1 (DSM ACC 2818), and 39D5 (DSM ACC 2930);
   b) identifying and/or isolating those cells in the sample to which an antibody from step a), or humanized form or antigen binding fragment thereof have bound, thereby isolating and/or identifying homogenous mesenchymal stem cells.

5. The method of claim 1, wherein the tissue is bone marrow, placenta, or adipose tissue.

6. The method of claim 2, wherein the tissue is bone marrow, placenta, or adipose tissue.

7. The method of claim 3, wherein the tissue is bone marrow, placenta, or adipose tissue.

8. The method of claim 1, wherein the antibody is produced from hybridoma cell line W1C3 (DSM ACC 2816).

9. The method of claim 1, wherein the antibody is produced from hybridoma cell line W7C6 (DSM ACC 2821).

10. The method of claim 1, wherein the antibody is produced from hybridoma cell line W5C4 (DSM ACC 2814).

11. The method of claim 1, wherein the antibody is produced from hybridoma cell line HEK-3D6 (DSM ACC 2817).

12. The method of claim 1, wherein the antibody is produced from hybridoma cell line W4A5 (DSM ACC 2571).

13. The method of claim 1, wherein the antibody is produced from hybridoma cell line W3D5 (DSM ACC 2815).

14. The method of claim 1, wherein the antibody is produced from hybridoma cell line W5C5 (DSM ACC 2813).

15. The method of claim 1, wherein the antibody is produced from hybridoma cell line 9A3G9 (DSM ACC 2820).

16. The method of claim 1, wherein the antibody is produced from hybridoma cell line 58B1 (DSM ACC 2819).

17. The method of claim 1, wherein the antibody is produced from hybridoma cell line F9-3C2F1 (DSM ACC 2818).

18. The method of claim 1, wherein the antibody is produced from hybridoma cell line 39D5 (DSM ACC 2930).

* * * * *